United States Patent
Naware et al.

(10) Patent No.: US 8,543,206 B2
(45) Date of Patent: Sep. 24, 2013

(54) EARLY DETECTION OF LEAD FAILURE USING AN IMPEDANCE HISTOGRAM

(75) Inventors: Mihir Naware, San Jose, CA (US); Cecilia Qin Xi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 515 days.

(21) Appl. No.: 12/823,870

(22) Filed: Jun. 25, 2010

(65) Prior Publication Data

US 2011/0319957 A1 Dec. 29, 2011

(51) Int. Cl.
*A61N 1/08* (2006.01)

(52) U.S. Cl.
USPC ............................................. 607/28

(58) Field of Classification Search
USPC .................................... 607/27–28
See application file for complete search history.

(56) References Cited

U.S. PATENT DOCUMENTS

| 4,899,750 | A | 2/1990 | Ekwall |
| 5,201,865 | A | 4/1993 | Kuehn |
| 2005/0059897 | A1* | 3/2005 | Snell et al. ............... 600/510 |
| 2009/0069708 | A1* | 3/2009 | Hatlestad et al. ......... 600/547 |
| 2010/0004714 | A1* | 1/2010 | Georgakopoulos et al. .... 607/44 |
| 2010/0030286 | A1 | 2/2010 | Goetz |
| 2010/0305633 | A1* | 12/2010 | Aziz ......................... 607/3 |
| 2012/0157861 | A1* | 6/2012 | Jarverud et al. ........... 600/486 |

* cited by examiner

*Primary Examiner* — Carl H Layno
*Assistant Examiner* — Paula J Stice
(74) *Attorney, Agent, or Firm* — Theresa Rayner; Steven M. Mitchell

(57) ABSTRACT

Testing lead conditions in an implantable medical device includes continuously sampling the impedance values of a lead associated with the implantable medical device. The sampling is conducted over a predetermined period of time. An impedance histogram is then generated using the sampled impedance values by separating each measured impedance value into a specific bin assigned to contain a particular range of impedance levels. The lead condition of the tested lead can then be determined based on one or more characteristics of the impedance histogram.

39 Claims, 7 Drawing Sheets

EARLY DETECTION OF LEAD FAILURE USING AN IMPEDANCE HISTOGRAM

FIELD OF THE DISCLOSURE

The present disclosure relates, in general, to implantable medical devices and, more particularly, to early detection of lead failure using an impedance histogram.

BACKGROUND

Implantable medical devices (IMDs) have become increasingly sophisticated and more capable over time. The initial implantable cardiac devices were typically pacemakers and/or implantable cardioverter-defibrillators (ICDs), which provided electrical pacing pulses to the heart at a generally fixed rate. As the technology has developed, more advanced pacing systems have been planted into patients. These more advanced systems are capable of providing pacing pulses to the heart only when the pacing system determines that the heart will not provide an intrinsic heart beat. Moreover, such advanced pacemakers are also able to adjust the pacing rate to accommodate different levels of physical activity and corresponding metabolic demand of the patient.

Typically, IMDs are equipped with sensors, which provide signals that are used by the IMD to determine the pacing rate. Such sensors include activity sensors, including accelerometers, metabolic rate sensors, including minute ventilation sensors, electrical sensors, including impedance sensors, pressure sensors, and the like. IMDs may also use the sensors to perform automatic testing functions by measuring various conditions of the heart.

When operating properly, an IMD will provide beneficial treatment to a patient. However, technical anomalies with the IMD device or any of its leads may cause the IMD to either fail to deliver appropriate treatment or deliver unnecessary treatment. Failure of pace/sense and high-voltage leads are a leading cause for the delivery of inappropriate therapies to patients that have IMDs. This problem has been identified by numerous physicians to be of paramount importance to the safety of the use of IMDs.

While daily high-voltage lead checks are able to determine high-voltage conductor failures, there are currently no existing methods to accurately detect intermittent low-voltage conductor failures. It is difficult to identify intermittent low-voltage conductor failures with a typical daily check because daily lead impedance checks are usually derived from the average value of the impedance data and do not consider the distribution of the impedance samples. Moreover, the daily check may not be taking measurements at times when the failures occur. For example, if the particular failure only occurs during a particular point during the cardiac cycle or between cardiac cycles, the daily check may not be testing at the exact time during which the failure occurs. Additionally, failures may occur at a certain time of day, for example, at night when the patient is lying down, or when the patient is making some specific type of physical movement. These various times or physical positions may trigger failures referred to as intermittent make/break connections. Intermittent make/break connections occur when shorts or open circuits occur within one or more of the leads due to a bad contact or when there is a make/break connection or contact between an intact lead and the cardiac tissue itself. This condition often leads to the production of sensing artifacts and the false detection of fast rhythms. Thus, it is unlikely that intermittent lead failures triggered by such transient conditions will be identified through periodic daily lead checks. Furthermore, because a tested vector is generally bipolar, it would not be possible to identify whether the tip conductor or the ring conductor has failed.

SUMMARY

Various aspects of the present disclosure are directed to the testing of lead conditions of a particular lead in an implantable medical device. The analysis begins by continuously sampling the impedance values of a lead or a combination of leads associated with the implantable medical device. The sampling is conducted over a predetermined period of time. An impedance histogram is then generated using the sampled impedance values by separating each measured impedance value into a specific bin assigned to contain a particular range of impedance levels. The lead condition of the tested lead or vector can then be determined based on one or more characteristics of the impedance histogram.

Additional aspects of the present disclosure are directed to a method for testing a lead condition in an implantable medical device. The method includes continuously sampling, over a predetermined period of time, impedance values of a lead associated with the implantable medical device, generating an impedance histogram using the sampled impedance values, and determining the lead condition based on one or more characteristics of the impedance histogram.

Further aspects of the present disclosure are directed to a system for testing lead condition in an implantable medical device. The system includes means for continuously sampling, over a predetermined period of time, impedance values of a lead associated with the implantable medical device, means for generating an impedance histogram using the sampled impedance values, and means for determining the lead condition based on one or more characteristics of the impedance histogram.

Still further aspects of the present disclosure are directed to an IMD that includes at least one electrical lead, a programmable microcontroller coupled to the electrical lead and controlling operation of the IMD, a memory coupled to the programmable microcontroller, and an early lead failure detection module stored in the memory. When executed by the programmable microcontroller, the early lead failure detection module configures the IMD to continuously sample, over a predetermined period of time, impedance values of a lead associated with the implantable medical device, to generate an impedance histogram using the sampled impedance values, and to determine a lead condition based on one or more characteristics of the impedance histogram.

The foregoing has outlined rather broadly the features and technical advantages of the present teachings in order that the detailed description of the teachings that follows may be better understood. Additional features and advantages of the teachings will be described hereinafter which form the subject of the claims of the teachings. It should be appreciated by those skilled in the art that the conception and specific embodiment disclosed may be readily utilized as a basis for modifying or designing other structures for carrying out the same purposes of the present teachings. It should also be realized by those skilled in the art that such equivalent constructions do not depart from the spirit and scope of the teachings as set forth in the appended claims. The novel features which are believed to be characteristic of the teachings, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present teachings.

BRIEF DESCRIPTION OF THE DRAWINGS

For a more complete understanding of the present teachings, reference is now made to the following descriptions taken in conjunction with the accompanying drawing.

DETAILED DESCRIPTION

The following description includes the best mode presently contemplated for practicing the present teachings. The description is not to be taken in a limiting sense but is merely for the purpose of describing the general principles of the illustrative embodiments. The scope of the present teachings should be ascertained with reference to the claims. In the description that follows, like numerals or reference designators will refer to like parts or elements throughout.

Overview of Implantable Devices

Figure 1:
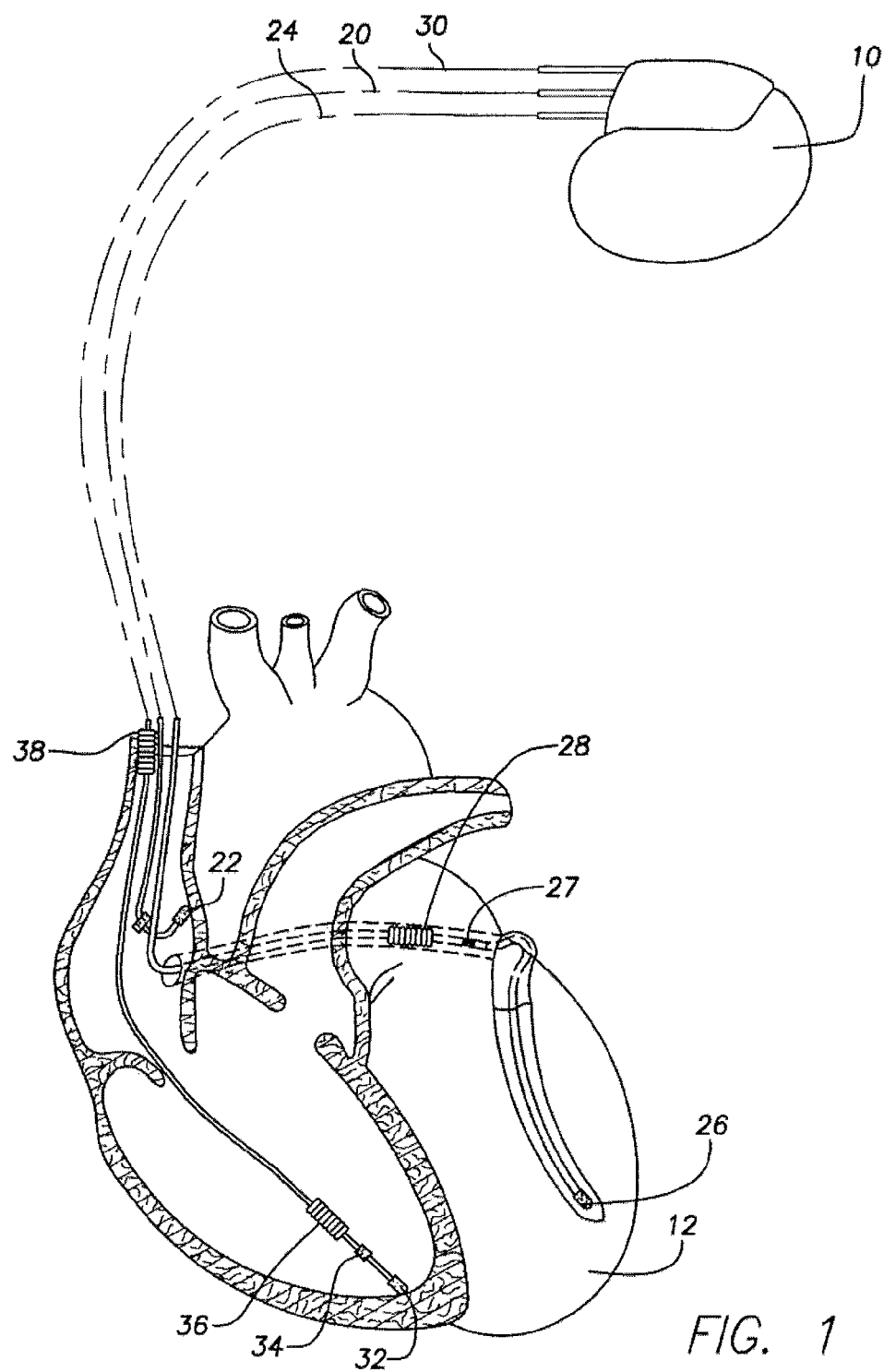
FIG. 1 is a diagram illustrating a medical device in electrical communication with the heart of a patient by way of three leads suitable for delivering multi-chamber stimulation and shock therapy.

With reference to FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage, and an atrial ring electrode 23.

To sense left atrial and ventricular cardiac signals and to provide left chamber pacing therapy, the stimulation device 10 is coupled to a quad pole lead 24 designed for placement in the latero or postero-lateral branch of the left ventricle via the coronary sinus. Accordingly, an exemplary quad pole lead 24 is designed to receive atrial and ventricular cardiac signals and to deliver left ventricular pacing therapy using at least a left ventricular distal electrode (D1) 26, mid first ring (M2) 29, mid second ring (M3) 27 and proximal ring (P4) 28. The inter-electrode spacing, in one embodiment, is 20 mm (D1-M2), 10 mm (M2-M3), and 17 mm (M3-P4). Thus, from tip to proximal the lead spans 47 mm. When the tip is pushed as far as anatomically possible in a coronary sinus branch, the proximal ring is often near the atrial-ventricular (AV) groove and sometimes even in the main coronary sinus or Great Cardiac Vein instead of the branch. The unipolar P4-RV coil sense vector, the bipolar M3-P4 sense vector, and sometimes additional unipolar and bipolar vectors, display both atrial and ventricular potentials on the electrogram.

As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart so as to place the right ventricular tip electrode 32 in the right ventricular apex so the RV coil electrode 36 is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "vibratory alert" signal (from a motor with an offset mass that can be provided in the device can), an additional electrode 31 can be provided in proximity to the device can.

Figure 2:
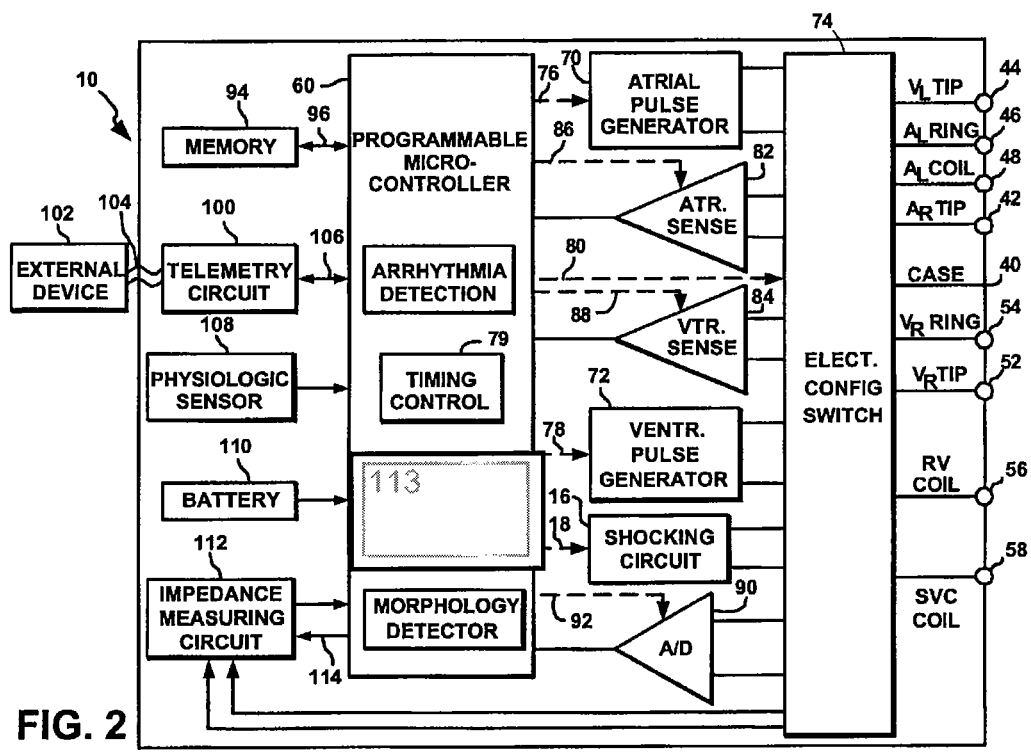
FIG. 2 is a block diagram illustrating an implantable medical device configured as a system in which the various embodiments of the present teachings may operate.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. The stimulation device 10 is configured as a system in which the various embodiments of the present teachings may operate. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, (FIG. 1) for shocking purposes. The housing 40 further includes a connector (not shown) having terminals, 42, 44, 46, 48, 52, 54, 56 and 58 (shown schematically and, for convenience, the names of the electrodes to which they are connected are shown next to the terminals).

As such, to achieve right atrial sensing and pacing, the connector includes at least a right atrial tip terminal (RA TIP) 42 adapted for connection to the atrial tip electrode 22 (FIG. 1) and a right atrial ring (RA RING) electrode (not shown) adapted for connection to the right atrial ring electrode 23 (FIG. 1). To achieve left chamber sensing, pacing and shocking, the connector includes at least a left ventricular tip terminal (LV TIP) 44, a left atrial ring terminal (LA RING) 46, and a left atrial shocking terminal (LA COIL) 48, which are adapted for connection to the left ventricular ring electrode 26 (FIG. 1), the left atrial tip electrode 27 (FIG. 1), and the left atrial coil electrode 28 (FIG. 1), respectively. To support right chamber sensing, pacing and shocking, the connector further includes a right ventricular tip terminal (RV TIP) 52, a right ventricular ring terminal (RV RING) 54, a right ventricular shocking terminal (RV COIL) 56, and an SVC shocking terminal (SVC COIL) 58, which are adapted for connection to the right ventricular tip electrode 32 (FIG. 1), right ventricular ring electrode 34 (FIG. 1), the RV coil electrode 36 (FIG. 1), and the SVC coil electrode 38 (FIG. 1), respectively. To provide the "vibratory alert" signal, a vibratory alert unit 122 generates a signal for an additional terminal (not shown) for connection to the vibratory alert electrode 31 (FIG. 1). In one embodiment, the vibratory alert will alert the patient, and then a home monitor can be used to transfer the information associated with the alert from the device 10 to an attending medical professional, who can take the appropriate clinical action.

At the core of the stimulation device 10 is a programmable microcontroller 60, which controls the various modes of stimulation therapy. As is well known in the art, the microcontroller 60 (also referred to as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. The microcontroller 60 includes the ability to process or monitor input signals (data) as controlled by program code stored in a designated block of the memory. The details of the design and operation of the microcontroller 60 are not critical to the present teachings. Rather, any suitable microcontroller 60 may be used that carries out the functions described. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20 (FIG. 1), the right ventricular lead 30 (FIG. 1), and/or the quad pole lead 24 (FIG. 1) via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 that controls the timing of such stimulation pulses (e.g., pacing rate, atrioventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., as is well known in the art. The switch 74 includes multiple switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20 (FIG. 1), the quad pole lead 24 (FIG. 1), and the right ventricular lead 30 (FIG. 1), through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers and may receive control signals 86, 88 from the controller 60. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, band pass filtering, and a threshold detection circuit, as known in the art, to selectively sense the cardiac signal of interest. The automatic gain control enables the device 10 to effectively address the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks).

Cardiac signals are also applied to the inputs of an analog-to-digital (A/D) data acquisition system 90. The data acquisition system 90 is configured to acquire intra-cardiac electrogram (IEGM) signals, convert the raw analog data into a digital signal, and store the digital signals for later processing and/or telemetric transmission to an external device 102. The data acquisition system 90 is coupled to the right atrial lead 20 (FIG. 1), the quad pole lead 24 (FIG. 1), and the right ventricular lead 30 (FIG. 1) through the switch 74 to sample cardiac signals across any pair of desired electrodes. The controller 60 controls the data acquisition system via control signals 92.

The microcontroller 60 is further coupled to a memory 94 by a suitable data/address bus 96. The programmable operating parameters used by the microcontroller 60 are stored and modified, as required, in order to customize the operation of the stimulation device 10 to suit the needs of a particular patient. The memory 94 stores lead condition templates 123, and lead condition detection modules 124 which, when used by the microcontroller 60, provide the operational functions of the implantable stimulation device 10, as described in more detail below. Additional operating parameters and code stored on the memory 94 define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, trans-telephonic transceiver, a diagnostic system analyzer, or even a cellular telephone. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In one embodiment, the stimulation device 10 further includes a physiologic sensor 108, commonly referred to as a "rate-responsive" sensor because it adjusts pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 is capable of operating at low current drains for long periods of time, and is capable of providing high-current pulses (for capacitor charging) when the patient requires a shock pulse. The battery 110 also has a predictable discharge characteristic so that elective replacement time can be detected. In one embodiment, the device 10 employs lithium/silver vanadium oxide batteries. As further shown in FIG. 2, the device 10 has an impedance measuring circuit 112 enabled by the microcontroller 60 via a control signal 114.

In the case where the stimulation device 10 is intended to operate as an IMD, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left proximal ring electrode 28 (FIG. 1), the RV coil electrode 36 (FIG. 1), and/or the SVC coil electrode 38 (FIG. 1). As noted above, the housing 40 may function as an active electrode in combination with the RV coil electrode 36 (FIG. 1), or as part of a split electrical vector using the SVC coil electrode 38 (FIG. 1) or the left proximal ring electrode 28 (FIG. 1) (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The microcontroller 60 includes a morphology detector 120 for tracking various morphological features within electrical cardiac signals, including intervals between polarization events, elevations between polarization events, durations of polarization events and amplitudes of polarization events. The microcontroller 60 also includes an early lead failure detection module 113 which analyzes the lead-specific impedance measurements to determine early lead failure according to the disclosure herein.

The remaining figures, flow charts, graphs and other diagrams illustrate the operation and novel features of the stimulation device 10 as configured in accordance with exemplary embodiments of the present teachings. In the flow chart, the various process steps are summarized in individual "blocks." Such blocks describe specific actions or decisions made or carried out as the process proceeds. Where a microcontroller (or equivalent) is employed, the functional block diagrams provide the basis for a "VA coupling analysis process" that may be used by such a microcontroller (or equivalent) to adaptively select RPC settings in IMD patients. Those skilled in the art may readily write such a program based on the functional block diagrams and other descriptions presented herein.

Determining Lead Condition

In various aspects of the present disclosure, lead conditions will be determined by analyzing a histogram that has been populated using a stream of continuous lead impedances measured at a particular sampling rate over a given period of time. Impedance measurement in IMDs is well known in the art. Various aspect of the present disclosure may use streams of current or voltage pulses in order to implement such known methods to measure impedance. In such aspects of the disclosure, induced cross-talk on the V-sense and A-sense channels may be avoided by measuring impedance using a relatively small current or voltage pulse. For example, a current pulse no larger than 250 μA may be used with the pulse width no wider than about 14 micro-seconds. Of course, additional current pulse parameters may be used that will reduce the possibility of such cross-talk. Such smaller pulses will also not cause treatment to be applied to the patient. Therefore, impedance samples may be taken at virtually any time and for various lengths or durations.

Figure 3:
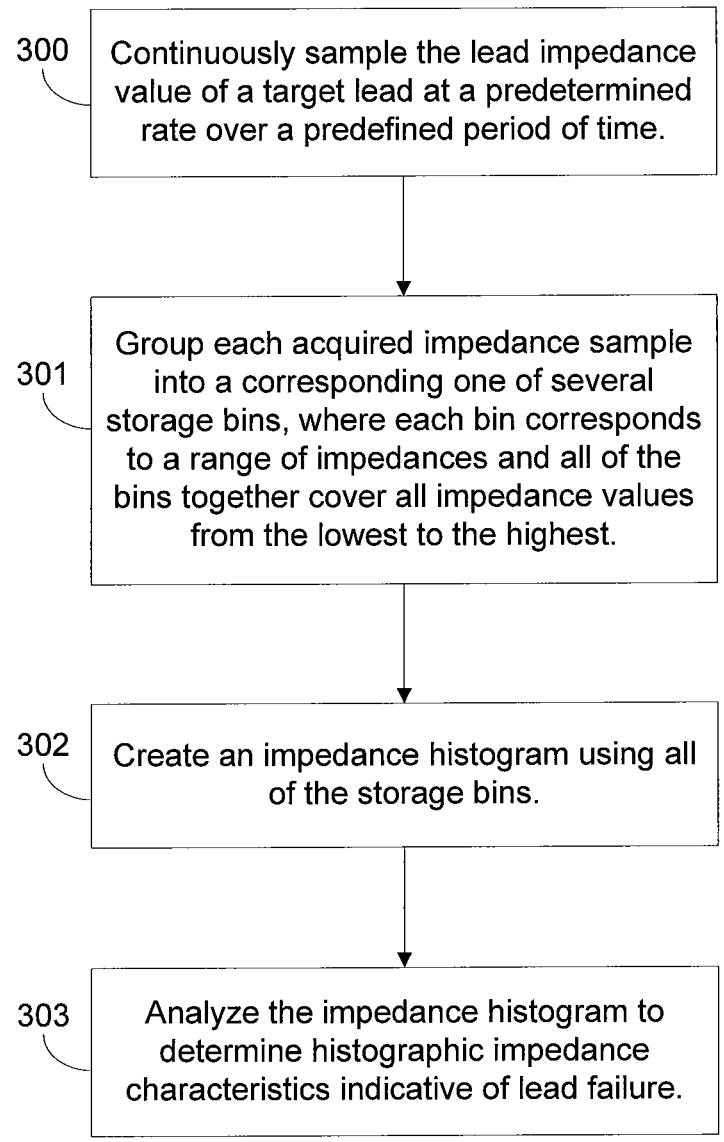
FIG. 3 is a functional block diagram illustrating example blocks executed to implement one aspect of the present disclosure.

FIG. 3 is a functional block diagram illustrating example blocks executed to implement one aspect of the present disclosure. In block 300, lead impedance values of a target lead are continuously sampled at a predetermined rate over a pre-defined period of time. The sampling rate may be dependent on the type of control hardware available within the IMD. For example, some IMDs may be capable of acquiring impedance samples at a rate of 64 samples per second, 128 samples per second, or the like. Additionally, the predefined period of time may be set to examine various stages of implantation of the device. For example, the samples along with their analysis may be conducted on an hourly basis, every 6 hours, daily, or the like. This predefined period of time may be set by the physician in order to accommodate the specific circumstances of the patient. When collecting the impedance data, the continual measurements will occur for at least 16 seconds at a time, which allows the measurements to be taken through a complete cardiac cycle or throughout the motion of the thoracic cavity during respiration. In this manner, impedance measurements will be available that reflect the physical state during the entire respiration cycle.

In block 301, each of the acquired impedance samples is grouped into a corresponding bin of a number of bins, wherein each bin corresponds to a range of impedances and all the bins together cover all impedance values from the lowest to the highest. An impedance histogram is created, in block 302, using all storage bins and the acquired samples collected therein. The impedance histogram will include a record for all of the bins which contain one or more impedance samples. In block 303, the impedance histogram will be analyzed to determine histographic impedance characteristics indicative of lead failure.

It should be noted that in additional aspects of the present disclosure, the testing and analysis described in FIG. 3 may be triggered by the detection of activity of the patient. This activity-induced analysis may be undertaken in order to detect any activity or exercise-induced lead failures that would be difficult to detect with a regularly time the check.

The impedance measurements taken for various embodiments of the present disclosure are used in the analysis as the actual measurement. Existing systems generally take measurements and calculate the averages over any given period of time. When averages are used, the minimum and maximum measurements may either be thrown out or significantly diminished because of the averaging. The various embodiments of the present disclosure utilize the actual measurements and make determinations or conclusions based on those measured minimums and maximums. For example, when an open circuit impedance is sporadically measured, it could mean that there is a make/break connection occurring somewhere in the lead at some point in time. In a system that uses averaged measurements, such extremes would be missed, thereby missing potential problems with the lead system.

In performing this lead analysis, the IMD will select a particular lead with which to perform the analysis. In one aspect of the present disclosure, the impedance samples and histographic analysis will be produced for each lead combination and a firmware-based assessment will be made of the stability of the RVtip and RVring conductors. In general, the vectors tested will be for the leads RVring-RVtip (bipolar), RVtip-CASE (unipolar), and RVring-CASE (unipolar). The unipolar vectors tested (e.g., the RVtip-CASE and RVring-CASE) may be used in order to identify tip or ring failures individually.

It should be noted that the various aspects of the present disclosure are not limited to measuring of impedance only with respect to RV leads, but may also test any other IMD leads, such as the RA leads, LV leads, and the like.

Figure 4:
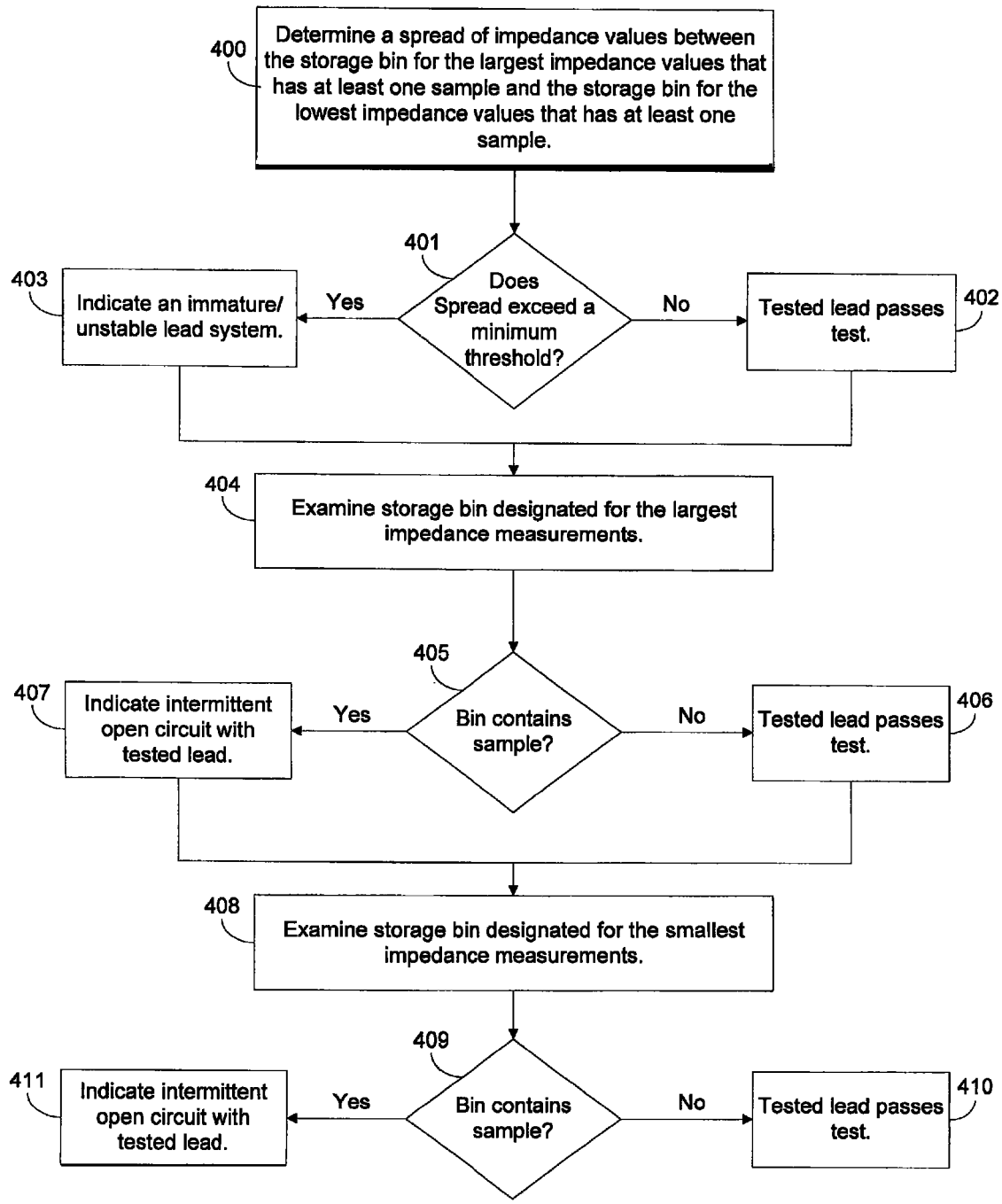
FIG. 4 is a functional block diagram illustrating example blocks executed to implement an analysis configured according to one aspect of the present disclosure.

FIG. 4 is a functional block diagram illustrating example blocks executed to implement an analysis configured according to one aspect of the present disclosure. In block 400, the spread of impedance values of the histogram is determined between the storage bin for the largest impedance values that has at least one sample and the storage bin for the smallest impedance values that has at least one sample. A determination is made, in block 401, whether the determined spread exceeds the minimum threshold value. If the minimum threshold is not exceeded, then, in block 402, the tested lead is indicated to have passed the determined spread test. Otherwise, the tested lead is indicated to be immature/unstable in block 403. Next, in block 404, the storage bin designated for the largest impedance measurements is examined. In block 405, a determination is made as to whether this bin contains any impedance samples. If not, then, in block 406, the tested lead is indicated to have passed the intermittent open circuit test. Otherwise, in block 407, the tested lead is indicated to have an intermittent open circuit problem or a problem with unacceptably high impedances. This type of problem may occur because of a failing lead or because of the mechanical motion of the heart causing intermittent open circuit anomalies. Next, in block 408, the storage bin designated for the smallest impedance measurements is examined. Again, in block 409, a determination is made as to whether this bin contains any samples. If not, then, in block 410, the tested lead is indicated to have passed the intermittent short circuit test. Otherwise, in block 411, the tested lead is indicated to have an intermittent short circuit problem or a problem with unacceptably low impedances. As noted above, this type of problem may occur because of a failing lead or because of the mechanical motion of the heart causing intermittent short circuit anomalies. The analysis will be used on each of the leads selected for testing by the IMD.

Figure 5:
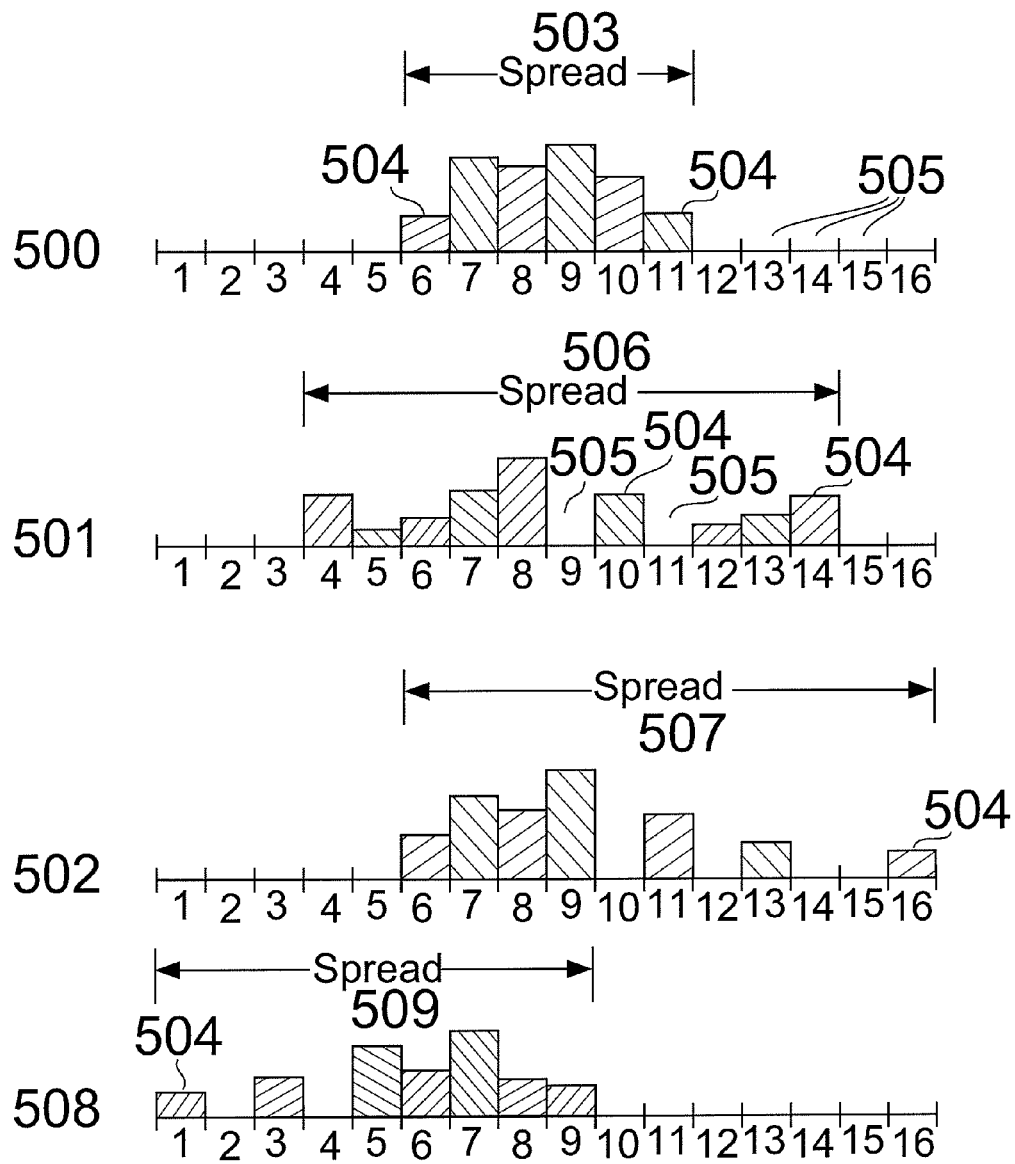
FIG. 5 is a diagram illustrating three histograms each generated by three different IMDs configured according to one aspect of the present disclosure.

FIG. 5 is a diagram illustrating four histograms 500, 501, 502, and 508 each generated by four different IMDs (not shown) configured according to one aspect of the present disclosure. After continuously sampling the lead impedance values, each impedance value is placed into the appropriate bin for its histogram. The histogram 500 illustrating rectangles 504 to represent the number of impedance values placed into the particular bin. The histogram 500 is shown having 16 impedance bins each designated to hold a sample within the impedance range assigned to the particular bin. For example, bin 1 is assigned to hold any impedance values measuring between 0 and 200 Ohms, while bin 16 is assigned to hold any impedance values measuring from 3000 Ohms and above. The bins 2-15 hold a range of impedances between 200 and 3000 Ohms. The height of each of the rectangles 504 represents the number of acquired impedance measurements of the target lead that fall within the bins' assigned values. The empty spaces along histogram 500 represent the empty bins 505.

When a lead system for an IMD is first implanted, there is a period of time when the leads may not operate as expected. This maturation period allows the leads to settle into their final position around and within the heart. It has been observed that immediately after implantation there may be some sensing anomalies. These anomalies may cause widely varying impedance measurements for the leads. As time progresses and the leads settle more into a final, stable location, the impedance measurements will tighten up into a more clustered and predictable spread. However, as these leads age, anomalies may again appear which cause a widening of the impedance spread for some or all of the leads in the lead system. In determining whether any given spread reflects a properly operating, mature and/or stable lead or lead having problems, a minimum threshold value is used for comparison. The minimum threshold value has been predetermined by the IMD manufacturer or clinic or physician based on analysis of historical data of spread measurements for properly operating, stable, and mature leads.

In operation, the early lead failure detection functionality provided by the IMD for which the histogram 500 has been created, will analyze the histogram 500 to determine the condition of the lead. The early lead failure detection functionality measures the impedance spread 503 of the histogram 500. The impedance spread 503 is the distance between the first bin containing at least one impedance value (bin 6) and the last bin containing at least one impedance value (bin 11). This impedance spread 503 illustrates a tight spread of impedance values for the target lead. As noted, a tight spread generally indicates a mature pacing/sensing lead system that is operating as expected. Thus, the target lead represented by the histogram 500 will be indicated as a mature lead system that is operating properly.

The histogram 501 is produced by another IMD analyzing another target lead located in the patient having the IMD. The calculated spread 506 of the histogram 501 reveals a much longer spread. The rectangles 504 are spread out further along the bins of the histogram 501 with some empty bins 505 interspersed between them. As analyzed by the early lead failure detection functionality, the larger spread 506 indicates this target lead is not a mature or stable pacing/sensing lead system. Therefore, the target lead that is the subject of the histogram 501 will be marked as needing attention. As the spreads are calculated by the early lead failure detection functionality, they will be compared against this minimum threshold value in order to determine whether the lead is performing within accepted criteria or not.

The histogram 502 is produced by yet another IMD analyzing another target lead. The calculated spread 507 is similar in length to the spread 506 of the histogram 501, which also exceeds the minimum threshold value. Thus, the length of the spread 507 indicates that the target lead is not a mature or stable lead. However, the histogram 502 also reveals an impedance value found in the last bin 16, which is the bin associated with the highest impedance values. The early lead failure detection functionality recognizes an impedance value in bin 16 as corresponding to a lead that experiences an intermittent open circuit. Therefore, the early lead failure detection functionality identifies this target lead as problematic not only because the spread 507 is longer than the minimum threshold value but also because of the impedance value found in bin 16.

The histogram 508 is produced by yet another IMD analyzing another target lead. The calculated spread 509 is similar in length to the spreads 506 and 507 of the histograms 501 and 502, which also exceed the minimum threshold value. Thus, the length of the spread 509 indicates that the target lead is not a mature or stable lead. However, the histogram 508 also reveals an impedance value found in the first bin 1, which is the bin associated with the lowest impedance values. The early lead failure detection functionality recognizes an impedance value in bin 1 as corresponding to a lead that experiences an intermittent short circuit. Therefore, the early lead failure detection functionality identifies this target lead as problematic not only because the spread 509 is longer than the minimum threshold value but also because of the impedance value found in bin 1.

A long-term analysis of the lead system may also be conducted by trending the spread calculations over a longer period. For example, by trending the spread over a one year period, the changes in the spread over that period of time may indicate whether the lead system is stable over a long-term period or whether there are long-term signs of an instability.

It should be noted that in additional aspects of the present teachings may be configured to have any different number of bins having various impedance ranges designated for each of the bins.

Having determined the status of the leads, there are a variety of actions that an IMD having such an early lead failure detection functionality may do with this information. A patient notification period may be utilized to alert the patient of some kind of anomaly in the lead system. The patient may then contact his or her physician for further investigation. Also, of course, the medical professionals may be notified through some kind of electronic messaging system that is associated with the IMD system. This information may also be stored on the IMD and then uploaded to an external monitoring device used by the physicians and medical professionals.

Selected embodiments of the present disclosure may also be used in determining lead maturation of a newly implanted IMD. After first implantation, an IMD and its leads may take some time before settling into their specific locations. Some of the pacing leads of the IMD are passively-fixed to the specific locations of the heart through the shape of the leads. Moreover with the passage of time, fibrosis/tissue in-growth will often lock these passively-fixed leads in place. However, during the time period between implantation and lead maturation, some of the readings or measurements performed by the various sensors and leads may not be entirely accurate. Thus, during some maturation periods, certain functionalities of the IMD may be disabled until those measurements are likely to be more reliable.

Figure 6:
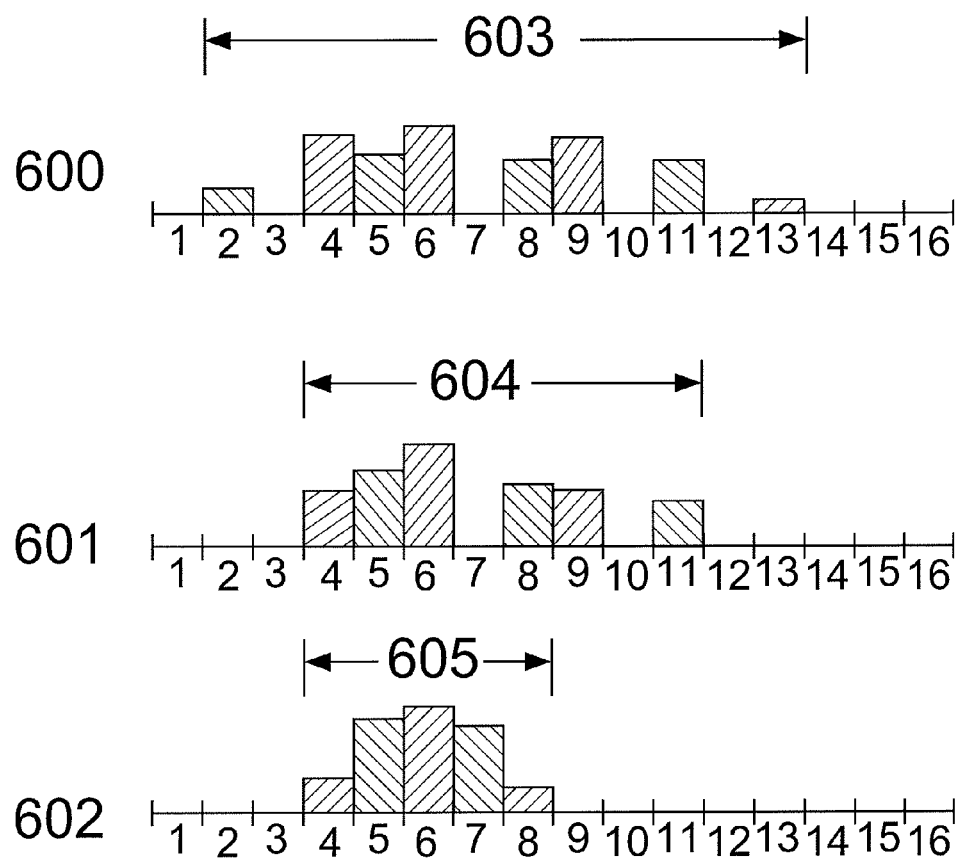
FIG. 6 is a diagram illustrating three histograms generated by an IMD (not shown) configured according to one aspect of the present disclosure.

FIG. 6 is a diagram illustrating three histograms 600-602 generated by an IMD (not shown) configured according to one aspect of the present disclosure. The histograms 600-602 reflect impedance measurements taken at three periods within a few months of implantation. The histogram 600 represents impedance measurements taken within two weeks of implantation. The histogram 601 represents impedance measurements taken a month and a half after implantation, and the histogram 602 represents impedance measurements taken at three months from implantation. The IMD will analyze the spread in each of the three histograms 600-602 to determine whether or not the leads have stabilized to a point where the lead maturation period may be ended. The spread 603 of the histogram 600 includes measurements that are somewhat scattered about the histogram bins. The wide span of the spread 603 indicates to the IMD that the system is still immature and the lead maturation period should continue. The spread 604 of the histogram 601 results in a narrower span of impedance bins. However, the spread 604 still indicates to the IMD that, while the lead system is becoming more stable, the lead maturation period should continue still. Finally, when the IMD analyzes the spread 605 of the histogram 602, the IMD determines that the span of impedance measurements have tightened considerably such that the span 605 is much more narrow. This narrowness indicates to the IMD that the lead system has become more mature, and, thus, the lead maturation period may be ended. Upon making this determination, the IMD can deactivate the lead maturation period restrictions on functionality and activate some of the impedance-based or measurement-based applications and functionalities for detecting various maladies, such as heart failure, pulmonary edema, and the like.

Figure 7:
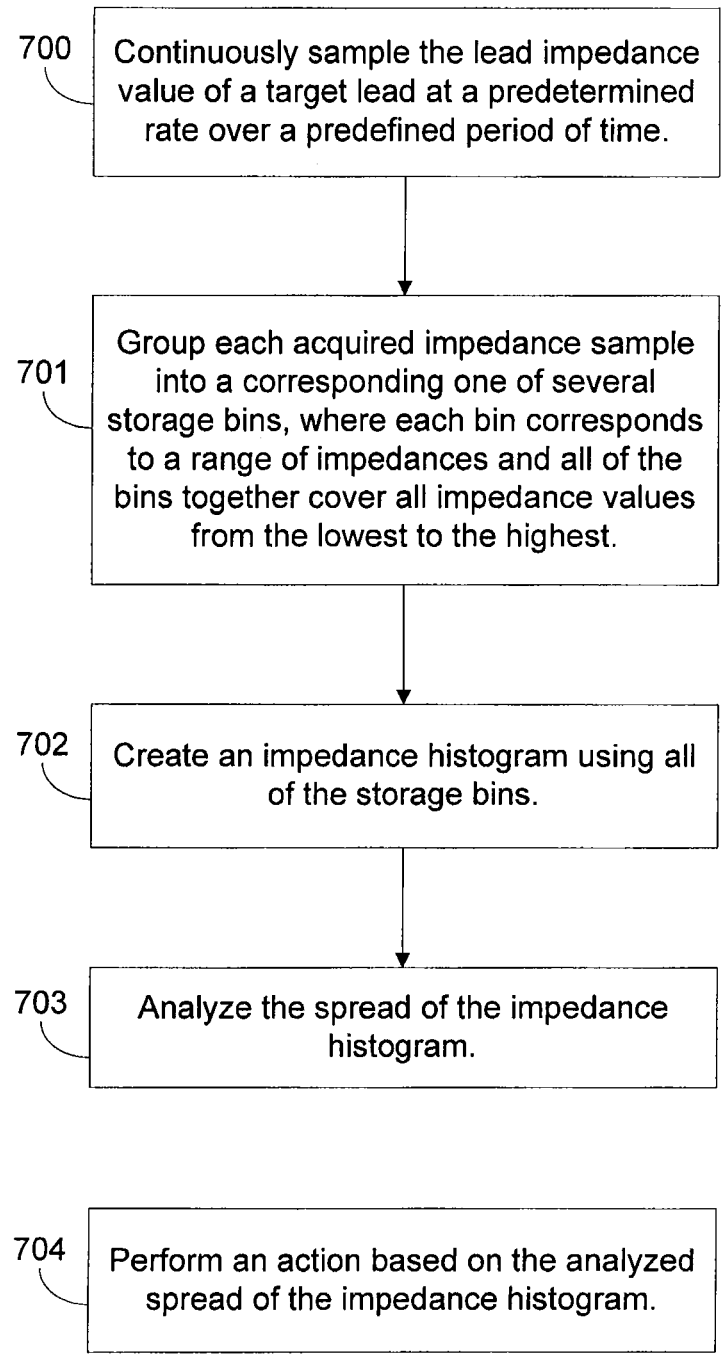
FIG. 7 is a functional block diagram illustrating example blocks executed to implement one aspect of the present disclosure.

FIG. 7 is a functional block diagram illustrating example blocks executed to implement one aspect of the present disclosure. In block 700, lead impedance values of a target lead are continuously sampled at a predetermined rate over a predefined period of time. Each of the acquired impedance samples is grouped into a corresponding bin of a number of bins, in block 701, wherein each bin corresponds to a range of impedances and all the bins together cover all impedance values from the lowest to the highest. An impedance histogram is created, in block 702, using all storage bins and the acquired samples collected therein. The impedance histogram will include a record for all of the bins which contain one or more impedance samples. In block 703, the spread of the impedance histogram will be analyzed. One or more actions may then be performed by the IMD, in block 704, based on the analyzed spread of the histogram. For example, if the IMD determines that the spread is too wide, it may make a determination that the lead system is unstable and deactivate certain functionalities. It may also, as noted above, determine that a recently implanted lead system is not yet mature enough for the lead maturation period to end. If the spread is more narrow, the IMD may determine that the lead system is mature and, in a recently implanted system, may deactivate the lead maturation period restrictions, thus, activating additional functionalities of the IMD.

As noted above, the early lead detection information may also be used by the IMD to control some of its own functionality. For example, the IMD may restrict or inhibit the delivery of inappropriate high-voltage therapy if any of the analyzed information indicates that an early lead failure is detected. Additionally, pulmonary edema monitoring may be disabled if lead failure is detected. Also, any cardiogenic impedance-based algorithms for heart failure detection may also be disabled if lead failure is detected. The various aspects of the present disclosure may use any number of these actions in conjunction with the resulting analysis derived from the early lead failure detection functionality described herein.

The methodologies described herein may be implemented by various means depending upon the application. For example, these methodologies may be implemented in hardware, firmware, software, or any combination thereof. For a hardware implementation, the processing units, including programmable microcontroller 60 (FIG. 2) may be implemented within one or more application specific integrated circuits (ASICs), digital signal processors (DSPs), digital signal processing devices (DSPDs), programmable logic devices (PLDs), field programmable gate arrays (FPGAs), processors, controllers, microcontrollers, microprocessors, electronic devices, other electronic units designed to perform the functions described herein, or a combination thereof.

For a firmware and/or software implementation, the methodologies may be implemented with modules (e.g., procedures, functions, and so on) that perform the functions described herein. Any machine or computer readable medium tangibly embodying instructions that may be in a form implantable or coupled to an implantable medical device may be used in implementing the methodologies described herein. For example, software code may be stored in a memory and executed by a processor. When executed by the processor, the executing software code generates the operational environment that implements the various methodologies and functionalities of the different aspects of the teachings presented herein. Memory may be implemented within the processor or external to the processor. As used herein the term "memory" refers to any type of long term, short term, volatile, nonvolatile, or other memory and is not to be limited to any particular type of memory or number of memories, or type of media upon which memory is stored.

The machine or computer readable medium that stores the software code defining the methodologies and functions described herein includes physical computer storage media. A storage medium may be any available medium that can be accessed by the processor of an implantable medical device. By way of example, and not limitation, such computer-readable media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. As used herein, disk and/or disc includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer readable media.

Although the present teachings and its advantages have been described in detail, it should be understood that various changes, substitutions and alterations can be made herein without departing from the spirit and scope of the present teachings as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present teachings, processes, machines, manufacture, compositions of matter, means, methods, or steps, presently existing or later to be developed that perform substantially the same function or achieve substantially the same result as the corresponding embodiments described herein may be utilized according to the present teachings. Accordingly, the appended claims are intended to include within their scope such processes, machines, manufacture, compositions of matter, means, methods, or steps.

What is claimed is:

1. A method for testing a lead condition in an implantable medical device, said method comprising:
   continuously sampling, over a predetermined period of time, impedance values of a lead associated with said implantable medical device;
   generating an impedance histogram using said sampled impedance values;
   determining, using a microprocessor, said lead condition of said lead based on one or more characteristics of said impedance histogram, wherein said determining comprises:
      examining a spread of impedance values of said impedance histogram;
      determining if the spread of impedance values is either within a minimum threshold value or exceeds said minimum threshold value;
      determining that said lead condition comprises a stable lead if said spread of impedance values is within a minimum threshold value; and
      determining that said lead condition comprises an unstable lead if said spread of impedance values exceeds said minimum threshold value; and
   following a determination that the lead condition comprises an unstable lead;
      if the implantable medical device is in a lead maturation period, maintaining the implantable medical device in the lead maturation period; and
      if the implantable medical device is in a post-lead maturation period, at least one of: restricting functionality of the implantable medical device, disabling functionality of the implantable medical device, notifying a user of an anomaly in the lead, marking the lead as needing attention, notifying a medical professional of the existence of an unstable lead, and storing data regarding the lead condition, uploading the data to an external monitoring device, and displaying data regarding the lead condition to a user.

2. The method of claim 1 wherein said impedance histogram includes a plurality of bins, each bin of said plurality representing a range of impedances, said plurality of bins covering all impedances measurable by said implantable medical device continually sampling said lead.

3. The method of claim 2 wherein said generating said impedance histogram comprising:
   determining an individual impedance value of each of said sampled impedance values; and
   placing each of said sampled impedance values into and associated one of said plurality of bins according to said individual impedance value.

4. The method of claim 1 wherein said predetermined time period is selectable by a medical professional managing care of said implantable medical device.

5. The method of claim 1 wherein said predetermined period of time is at least 16 seconds in duration.

6. The method of claim 1 wherein said determining said lead condition of said lead further comprises:

determining a highest impedance bin;
examining the highest impedance bin of said impedance histogram, said highest impedance bin defined to hold a high range of highest impedance values measureable by said implantable medical device; and
in response to said highest impedance bin containing at least one of said sampled impedance values, identifying said lead condition as comprising an intermittent open circuit.

7. The method of claim 1 wherein said determining said lead condition of said lead further comprises:
determining a lowest impedance bin;
examining the lowest impedance bin of said impedance histogram, said lowest impedance bin defined to hold a low range of lowest impedance values measureable by said implantable medical device; and
in response to said lowest impedance bin containing at least one of said sampled impedance values, identifying said lead condition as comprising an intermittent short circuit.

8. A method for testing a lead condition in an implantable medical device, said method comprising:
continuously sampling, over a predetermined period of time, impedance values of a lead associated with said implantable medical device;
generating an impedance histogram using said sampled impedance values;
determining, using a microprocessor, said lead condition of said lead based on one or more characteristics of said impedance histogram, wherein said determining comprises:
determining a highest impedance bin,
examining the highest impedance bin of said impedance histogram, said highest impedance bin defined to hold a high range of highest impedance values measureable by said implantable medical device, and
in response to said highest impedance bin containing at least one of said sampled impedance values, identifying said lead condition as comprising an intermittent open circuit; and
in response to identifying the lead condition as comprising an intermittent open circuit, at least one of: restricting and/or disabling functionality of the implantable medical device, and notifying a user that the lead condition comprises an intermittent open circuit.

9. A method for testing a lead condition in an implantable medical device, said method comprising:
continuously sampling, over a predetermined period of time, impedance values of a lead associated with said implantable medical device;
generating an impedance histogram using said sampled impedance values; and
determining, using a microprocessor, said lead condition of said lead based on one or more characteristics of said impedance histogram, wherein said determining comprises:
determining a lowest impedance bin;
examining the lowest impedance bin of said impedance histogram, said lowest impedance bin defined to hold a low range of lowest impedance values measureable by said implantable medical device; and
in response to said lowest impedance bin containing at least one of said sampled impedance values, identifying said lead condition as comprising an intermittent short circuit; and
in response to identifying the lead condition as comprising an intermittent short circuit, at least one of: restricting and/or disabling functionality of the implantable medical device, and notifying a user that the lead condition comprises an intermittent short circuit.

10. A method for testing a lead condition in an implantable medical device, said method comprising using a microprocessor to:
continuously sample, over a predetermined period of time, impedance values of a lead associated with said implantable medical device;
generate an impedance histogram using said sampled impedance values; and
determine said lead condition of said lead based on one or more characteristics of said impedance histogram, wherein said determining comprises:
determining a spread of said impedance values in said impedance histogram;
examining the spread of said impedance values in said impedance histogram;
determining whether said spread exceeds a predetermined maximum spread or whether said spread falls within a predetermined minimum spread;
when said spread exceeds the predetermined maximum spread, determining said lead condition comprises an immature lead; and
when said spread falls within the predetermined minimum spread, determining said lead condition comprises a mature lead and activating functionality the implantable medical device.

11. The method of claim 10 wherein the implantable medical device is in a lead maturation period, the method further comprising, when said spread exceeds a predetermined maximum spread, maintaining said implantable medical device in said lead maturation period.

12. The method of claim 10 wherein the implantable medical device is in a lead maturation period, and further comprising, when said spread exceeds a predetermined minimum spread, deactivating said lead maturation period.

13. The method of claim 10 further comprising deactivating at least one functionality of said implantable medical device based, at least in part, on said spread of impedance values.

14. The method of claim 10 further comprising activating at least one functionality of said implantable medical device based, at least in part, on said spread of impedance values.

15. A system for testing lead condition in an implantable medical device, said system comprising:
means for sampling using a continuous stream of voltage or current pulses throughout a predetermined period of time, impedance values of a lead associated with said implantable medical device, wherein the period of time includes at least a cardiac cycle;
means for generating an impedance histogram using said sampled impedance values;
means for determining said lead condition of said lead based on one or more characteristics of said impedance histogram;
means for examining a spread of impedance values of said impedance histogram;
means for determining if the spread of impedance values is either within a minimum threshold value or exceeds said minimum threshold value;
means, executable in response to said spread of impedance values being within said minimum threshold value, for identifying said lead condition as comprising a stable lead; and means, executable in response to said spread of impedance values exceeding said minimum threshold value, for identifying said lead condition as comprising an unstable lead.

16. The system of claim 15 further comprising:
means for examining a highest impedance bin of said impedance histogram, said highest impedance bin defined to hold a high range of highest impedance values measureable by said implantable medical device;
means, executable in response to said highest impedance bin containing at least one of said sampled impedance values, for identifying said lead condition as comprising an intermittent open circuit.

17. The system of claim 15 further comprising:
means for examining a lowest impedance bin of said impedance histogram, said lowest impedance bin defined to hold a low range of lowest impedance values measureable by said implantable medical device; and
means, executable in response to said lowest impedance bin containing at least one of said sampled impedance values, for identifying said lead condition as comprising an intermittent short circuit.

18. A system for testing lead condition in an implantable medical device, said system comprising:
means for sampling using a continuous stream of voltage or current pulses throuphput a predetermined period of time, impedance values of a lead associated with said implantable medical device, wherein the period of time includes at least a cardiac cycle;
means for generating an impedance histogram using said sampled impedance values;
means for determining said lead condition of said lead based on one or more characteristics of said impedance histogram;
means for examining a spread of said impedance values in said impedance histogram;
means for determining whether said spread exceeds a predetermined maximum spread or whether said spread falls within a predetermined minimum spread;
means, executable in response to said spread exceeding the predetermined maximum spread, for identifying said lead condition as comprising an immature lead; and
means, executable in response to said spread falling within the predetermined minimum spread, for identifying said lead condition as comprising a mature lead.

19. The system of claim 18 wherein said predetermined time period is selectable by a medical professional managing care of said implantable medical device.

20. The system of claim 18 wherein said implantable medical device is programmed to be in a lead maturation period, the system further comprising a means, executable in response to said spread exceeding a predetermined maximum spread, for maintaining said implantable medical device in said lead maturation period.

21. The system of claim 18 wherein said implantable medical device is programmed to be in a lead maturation period, the system further comprising a means, executable in response to said spread falling within a predetermined minimum spread, for deactivating said lead maturation period.

22. The system of claim 18 further comprising:
means for examining a highest impedance bin of said impedance histogram, said highest impedance bin defined to hold a high range of highest impedance values measureable by said implantable medical device;
means, executable in response to said highest impedance bin containing at least one of said sampled impedance values, for identifying said lead condition as comprising an intermittent open circuit.

23. The system of claim 18 further comprising:
means for examining a lowest impedance bin of said impedance histogram, said lowest impedance bin defined to hold a low range of lowest impedance values measureable by said implantable medical device; and
means, executable in response to said lowest impedance bin containing at least one of said sampled impedance values, for identifying said lead condition as comprising an intermittent short circuit.

24. A system for testing lead condition in an implantable medical device, said system comprising:
means for sampling using a continuous stream of voltage or current pulses throughout a predetermined period of time, impedance values of a lead associated with said implantable medical device, wherein the period of time includes at least a cardiac cycle;
means for generating an impedance histogram using said sampled impedance values;
means for determining said lead condition of said lead based on one or more characteristics of said impedance histogram;
means for examining a spread of said impedance values in said impedance histogram; and
means for deactivating at least one functionality of said implantable medical device based, at least in part, on said spread of impedance values.

25. The system of claim 24 further comprising:
means for activating at least one functionality of said implantable medical device based, at least in part, on said spread of impedance values.

26. An implantable medical device (IMD) comprising:
at least one electrical lead;
a programmable microcontroller coupled to said at least one electrical lead, said programmable microcontroller controlling operation of said IMD;
a memory coupled to said programmable microcontroller; and
an early lead failure detection module stored in the memory, wherein, when executed by the programmable microcontroller, said early lead failure detection module configures said IMD:
to continuously sample, over a predetermined period of time, impedance values of a lead associated with said implantable medical device;
to generate an impedance histogram using said sampled impedance values;
to determine a lead condition of said lead based on one or more characteristics of said impedance histogram;
to examine a spread of impedance values of said impedance histogram, wherein:
in response to said spread of impedance values being within a minimum threshold value, said lead condition comprises a stable lead; and
in response to said spread of impedance values exceeding said minimum threshold value, said lead condition comprises an unstable lead.

27. The IMD of claim 26 wherein said early lead failure detection module further configures said IMD:
to examine a lowest impedance bin of said impedance histogram, said lowest impedance bin defined to hold a low range of lowest impedance values measureable by said implantable medical device; and to identify said lead condition as comprising an intermittent short circuit in response to said lowest impedance bin containing at least one of said sampled impedance values.

28. The IMD of claim 26 wherein said early lead failure detection module further configures said IMD:
to examine a highest impedance bin of said impedance histogram, said highest impedance bin defined to hold a high range of highest impedance values measureable by said implantable medical device; and
to identify said lead condition as comprising an intermittent open circuit in response to said highest impedance bin containing at least one of said sampled impedance values.

29. An implantable medical device (IMD) comprising:
at least one electrical lead;
a programmable microcontroller coupled to said at least one electrical lead, said programmable microcontroller controlling operation of said IMD;
a memory coupled to said programmable microcontroller; and
an early lead failure detection module stored in the memory, wherein, when executed by the programmable microcontroller, said early lead failure detection module configures said IMD:
to continuously sample, over a predetermined period of time, impedance values of a lead associated with said implantable medical device;
to generate an impedance histogram using said sampled impedance values;
to determine a lead condition of said lead based on one or more characteristics of said impedance histogram;
to examine a highest impedance bin of said impedance histogram, said highest impedance bin defined to hold a high range of highest impedance values measureable by said implantable medical device;
to identify said lead condition as comprising an intermittent open circuit in response to said highest impedance bin containing at least one of said sampled impedance values.

30. An implantable medical device (IMD) comprising:
at least one electrical lead;
a programmable microcontroller coupled to said at least one electrical lead, said programmable microcontroller controlling operation of said IMD;
a memory coupled to said programmable microcontroller; and
an early lead failure detection module stored in the memory, wherein, when executed by the programmable microcontroller, said early lead failure detection module configures said IMD:
to continuously sample, over a predetermined period of time, impedance values of a lead associated with said implantable medical device;
to generate an impedance histogram using said sampled impedance values;
to determine a lead condition of said lead based on one or more characteristics of said impedance histogram;
to examine a lowest impedance bin of said impedance histogram, said lowest impedance bin defined to hold a low range of lowest impedance values measureable by said implantable medical device; and
to identify said lead condition as comprising an intermittent short circuit in response to said lowest impedance bin containing at least one of said sampled impedance values.

31. The IMD of claim 30 wherein said predetermined time period is selectable by a medical professional managing care of said implantable medical device.

32. The IMD of claim 30 wherein said predetermined period of time comprises a length of at least 16 seconds.

33. An implantable medical device (IMD) comprising:
at least one electrical lead;
a programmable microcontroller coupled to said at least one electrical lead, said programmable microcontroller controlling operation of said IMD;
a memory coupled to said programmable microcontroller; and
an early lead failure detection module stored in the memory, wherein, when executed by the programmable microcontroller, said early lead failure detection module configures said IMD:
to continuously sample, using a continuous stream of pulses throughout a predetermined period of time, impedance values of a lead associated with said implantable medical device, wherein the predetermined period of time includes at least a cardiac cycle,
to generate an impedance histogram using said sampled impedance values,
to determine a lead condition of said lead based on one or more characteristics of said impedance histogram, and
to examine a spread of said impedance values in said impedance histogram.

34. The IMD of claim 33 wherein, in response to said spread exceeding a predetermined maximum spread, said early lead failure detection module further configures said IMD to identify said lead condition as comprising an immature lead.

35. The IMD of claim 33 further comprising said implantable medical device being in a lead maturation period, wherein in response to said spread exceeding a predetermined maximum spread, said early lead failure detection module further configures said IMD to maintain said IMD in said lead maturation period.

36. The IMD of claim 33 wherein, in response to said spread falling within a predetermined minimum spread, said early lead failure detection module further configures said IMD to identify said lead condition as comprising a mature lead.

37. The IMD of claim 33 further comprising said implantable medical device being in a lead maturation period, wherein, in response to said spread falling within a predetermined minimum spread, said early lead failure detection module further configures said IMD to deactivate said lead maturation period.

38. The IMD of claim 33 wherein said early lead failure detection module further configures said IMD to deactivating at least one functionality of said implantable medical device based, at least in part, on said spread of impedance values.

39. The IMD of claim 33 wherein said early lead failure detection module further configures said IMD to activate at least one functionality of said implantable medical device based, at least in part, on said spread of impedance values.

* * * * *